United States Patent [19]
Hablov et al.

[11] Patent Number: 5,448,501
[45] Date of Patent: Sep. 5, 1995

[54] ELECTRONIC LIFE DETECTION SYSTEM

[75] Inventors: Dimitri V. Hablov; Oleg I. Fisun; Lev N. Lupichev; Viktor V. Osipov; Viktor A. Schestiperov, all of Moscow, Russian Federation; Richard Schimko, Berlin, Germany

[73] Assignee: BORUS Spezialverfahren und-geräte im Sondermachinenbau GmbH, Berlin, Germany

[21] Appl. No.: 162,583

[22] Filed: Dec. 3, 1993

[30] Foreign Application Priority Data

Dec. 4, 1992 [DE] Germany .................. 42 41 664.7

[51] Int. Cl.$^6$ ............................................. G01S 17/32
[52] U.S. Cl. .................. 364/517; 364/413.03; 128/671; 128/653.1; 342/28; 329/322; 329/354; 332/129
[58] Field of Search .................. 364/413.06, 413.03, 364/517; 340/552, 571, 572, 573; 128/653 R, 653.1, 671, 716, 721; 329/322, 354; 332/129, 163; 342/28

[56] References Cited

U.S. PATENT DOCUMENTS 4,958,638 9/1990 Sharpe et al. .................. 128/653 R

OTHER PUBLICATIONS

Chuang et al; "Automatic Clutter-Canceler for Microwave Life-Detection Systems," IEEE Trans. Instrumentation and Measurement, vol. 40 No. 4 Aug. 1991.
Masuyama et al; "Detection of Objects Buried in Wet Snowpack by an FM-CW Radars"; IEEE Tran on Geoscience and Remote Sensing; vol. 29ISU.2; 03191.
Yamaguchi et al; "FM-CW Radrr Applied to the Detection of Buried Objects in Showpack"; IEEE Confrence Paper, 1990 Symposium Digest. Antennas and Propagation; vol. 4, pp. 2072.

*Primary Examiner*—Ellis B. Ramirez
*Assistant Examiner*—Kamini S. Shah
*Attorney, Agent, or Firm*—Chilton, Alix & Van Kirk

[57] ABSTRACT

The invention relates to an electronic life detection system, in particular for the searching for buried persons and the surveillance of buildings, having a microwave transmitting/receiving device for generating and radiating microwaves into an area to be investigated and for registering the microwave signal reflected from the area under surveillance and modulated with the frequencies corresponding to the life functions of any living beings present in the area, which device has a first signal-conditioning device, and a second signal-conditioning device.

10 Claims, 8 Drawing Sheets

Fig. 6

ELECTRONIC LIFE DETECTION SYSTEM

FIELD OF THE INVENTION

The invention relates to an electronic life detection system using microwaves reflected by a living being and modulated by its body oscillations, having a microwave transmitting/receiving device for generating and radiating the microwaves and also for receiving and conditioning the reflection signal by elimination of the reflected signal contained in unmodulated form in the received signal by a first signal-conditioning device and also having an indicating device for outputting the indication results.

BACKGROUND OF THE INVENTION

It is known to use the wave field emanating from a person in an analogous way as a detection field.

For example, such an electronic surveillance system based on the infrared radiation emanating from persons is described in DE 38 32 428 A1.

Finally, the use of microwave radiation for movement detection on open land or inside premises which is based on the modulation of a microwave beam by objects moving in the area exposed to the radiation is also known.

Furthermore, also known are search devices which operate with microwaves and are used for locating persons cut off from the outside world by earthquakes or avalanches.

The use of microwaves for locating buried persons is based on the fact that microwaves are to some extent capable of penetrating rubble and rock debris and that the reflected components exhibit different characteristics, depending on the material.

K. Chen et al. "An X-band microwave life-detection system", IEEE Transactions on biomedical engineering, Vol. BME 33, No. 7, July 1986 discloses such an electronic life detector, operating with microwaves, as mentioned above.

In the case of this electronic life detector, microwaves of a certain frequency are continuously radiated into a spatial area to be investigated.

If there is a living person there, the signal reflected from the scanned area has an unmodulated component and a component modulated by the body functions, specifically breathing and heartbeat, of the person cut off from the outside world. The unmodulated component of the reflected signal is eliminated by a compensation loop which can be controlled in its phase and attenuation constant.

The informational content of the modulated component of the reflected signal is thus selected by a phase comparison with the emitted (scanning) signal.

In the cited publication there is also described a modification of the process suitable for contactless patient monitoring which makes do without a directional aerial and with an output power of 0.1 mW.

This known apparatus is, however, suitable only to a limited extent for use under unfavourable conditions in which the received reflection signals are very weak and/or fluctuating greatly in their intensity, and in particular for a preventive surveillance of buildings.

Furthermore, U.S. Pat. No. 4,967,751 discloses an apparatus in which the microwaves radiating through a living body are subjected to a frequency analysis. This process is not suitable, however, for the detection of living beings, since a building or an area where people are buried is not usually accessible from opposing sides.

SUMMARY OF THE INVENTION

The invention is therefore based on the object of providing an electronic life detection system of the generic type mentioned at the beginning which, by virtue of extended application capabilities, is suitable under unfavourable conditions and, in particular, for the surveillance of buildings.

This object is achieved by an electronic life detection system using microwaves reflected by a living being and modulated by its body oscillations, having a microwave transmitting/receiving device for generating and radiating the microwaves and also for receiving and conditioning the reflection signal by elimination of the reflected signal contained in unmodulated form in the received signal by a first signal-conditioning device and also having an indicating device for outputting the indication results, characterized by a second signal-conditioning device, which is arranged downstream of the microwave transmitting/receiving device and subjects the microwave signal processed by the first signal-conditioning device to a frequency analysis.

The invention embraces a recognition of the idea that the presence or identity of persons or other living beings can be detected on the basis of the modulated component of the reflected microwave signal if it is subjected to a frequency analysis. The frequency spectrum forms a type of "electronic fingerprint" of the living being with characteristic features, which on the one hand permits a detection by comparison with stored patterns, but on the other hand also permits a distinction between different living beings.

It can be advantageously used for increasing accuracy in the detection of living beings, preferably persons, present in buildings without authorization or else in recognising the identity of living beings.

In the case of the electronic life detection system according to the invention, the receiving circuit is designed such that it permits a measurement even in the case of very small signal-to-noise ratios and without overdriving.

Consequently, an unfalsified sensing of the modulation frequencies (i.e. consequently of the underlying body-oscillation frequencies) of living beings present in the area to be investigated is possible, and consequently—depending on the area of application—so too is their identification and/or the establishing of their physical condition.

For this purpose, advantageously an automatic sensitivity control is provided.

Furthermore, the system is designed such that the microwave transmitting/receiving device is followed downstream by a signal conditioning device, which subjects the received signal, pre-conditioned within the receiving device, to a frequency and/or correlation analysis.

The system preferably has—in particular if used for surveillance tasks in which it is required to distinguish between persons or detect their current physical condition—a first and second memory device for storing model or actual signal values respectively and a comparator unit for comparing the signal quantities taken from the memory devices and for outputting a signal characterizing the result of the comparison to an indicating device.

For carrying out the data comparison, it is of particular advantage if the signals determined, sensed in the time domain, are subjected to a frequency analysis, in particular in the form of a fast Fourier transformation (FFT). The FFT-conditioned signals in this case respectively represent a frequency spectrum.

The accuracy of detection is increased in an advantageous way by the scanning of a building to be subjected to surveillance being performed by scanning in the sense of a spatial scanning with a highly concentrated microwave beam by means of a correspondingly designed directional aerial with variable alignment. The changing of the alignment of the aerial is in this case preferably performed electronically.

According to a preferred configuration of the invention, the electronic surveillance system for the mobile surveillance of a plurality of buildings for the purpose of detecting persons who have entered one or more of these buildings without authorization has first and second memory devices, the memory addresses $Z_1$ to $Z_n$ of which are assigned to the individual buildings to be subjected to surveillance and the memory content of which comprises signal quantities relating to building-specific features for the normal situation, premises-related security measures for the event of unauthorized use of a building, time-variable occupancy and use criteria, positional data of the buildings in the respective area of land and of the location of a vehicle for carrying out the mobile surveillance and building-specific additional information.

After compensation of their unmodulated component and automatic level setting, the microwaves reflected from the building and picked up by the mobile detector of the surveillance system are subjected to a fast Fourier transformation and then compared with the signal quantities available in the memory device and assigned to the same building or section of building or land.

In the signal processing unit, a device is provided for the optional accumulation of a plurality of measuring signals, which is put into operation if the signal-to-noise ratio of an individual measurement is not adequate for obtaining a Fourier transform which is comparable with respect to noise with the one which is stored.

The memory devices are designed such that they can be cyclically driven by a multiplexer. Putting the sending and receiving devices into operation and reading out the building-specific signal quantities from the memory devices of the surveillance system is always performed whenever the vehicle used for mobile surveillance has taken up a location which is defined and can be checked by a separate control system.

For setting off an alarm owing to persons present in the building without authorization, it is necessary that the deviation of the stored (model) signal quantities from the detected (actual) signal quantities satisfies predetermined criteria or—more simply—exceeds a certain amount.

A comparator unit, operating in an advantageous way by a correlation method, and a suitably dimensioned threshold stage bring about the required setting off of the alarm, for instance on an indicating device, when there is a corresponding signal-quantity deviation. For the reading out of the signal data, in particular of the positional data for the individual buildings, from the second memory device there is provided a multiplexer, which is driven by a random generator. As a result, in an advantageous way, a manipulation of the sequence of surveillance of the individual premises—and consequently of the constitution of a control journey—is avoidable and results in an increase in the effectiveness of the surveillance measures.

Advantageous further developments of the invention are characterized in subclaims and/or are presented in more detail below together with the description of the preferred configuration of the invention with reference to the figures.

DESCRIPTION OF THE PREFERRED EMBODIMENTS

Figure 1A:
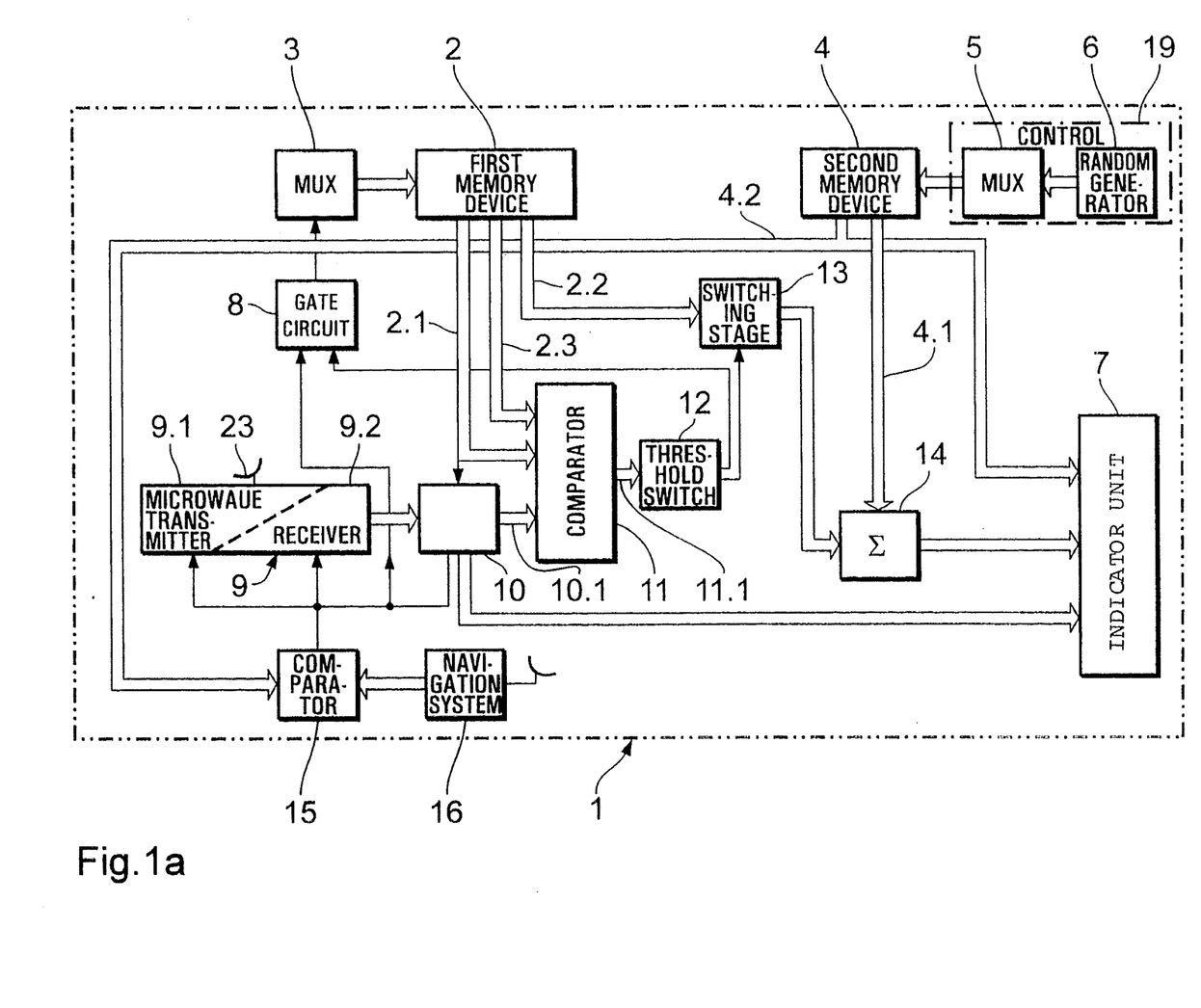
FIG. 1a shows a block diagram of a preferred embodiment of the invention in schematized representation.

In FIG. 1a a block diagram of an exemplary embodiment of the electronic surveillance system is represented in schematized form, the main elements of which are a microwave transmitting/receiving device 9 with a transmitter 9.1 and a receiver 9.2, a first and a second memory device 2 and 4, in which the main surveillance-specific quantities of data of individual buildings to be subjected to surveillance are stored, and a comparator unit 11.

By means of an aerial 23, the transmitter 9.1 transmits into the area to be subjected to surveillance a surveillance signal which, partially reflected in the said area, is fed as a received signal via the aerial 23 to the receiver 9.2. From there, it passes to a conditioning unit, which obtains from it an actual signal quantity 10.1.

The first memory device 2 sends signal quantities 2.1 and 2.3 (building features under normal conditions and current occupancy criteria for a particular building $Z_x$) to the comparator unit 11, which is also sent the actual signal quantity 10.1.

The comparator unit is designed such that it executes a comparison of the model signal quantities with the associated actual signal quantity by a correlation method on the basis of frequency spectra formed from the signal quantities by fast Fourier transformation.

The result of the comparison is fed to a threshold switch 12. The exceeding of a degree of permissible deviation between the model and actual signal quantities characterizing the building to be subjected to surveillance, predetermined in advance to avoid any false alarm caused by measuring errors, results in activation of the switching stage 13, by which the signal quantities 2.2 (premises-related security measures from the first memory device 2) and 4.1 (building-specific additional information from the second memory device 4) pass via a summing circuit 14 to the alarm-signalling device or indicating unit 7, where the setting off of an alarm is performed with a simultaneous display of all information relevant for service personnel (cf. the description with respect to FIG. 5).

The reading out of the signal quantities from the memory addresses assigned to the individual buildings $Z_1$ to $Z_n$ is performed from the two memory devices 2 and 4 in each case by an external control 3 and 19, respectively.

The control 19 for the memory device 4 with the signal quantities 4.2 (positional data of the buildings to be subjected to surveillance) comprises a cyclical multiplexer 5 and a random generator 6 driving the latter. The selection of the building to undergo a control check first and of the buildings subsequently to undergo control checks is in this way performed randomly and, advantageously, in a way safeguarded against any manipulation.

The positional data 4.2 are displayed on the indicating unit 7 and at the same time fed to a further comparator unit 15, which by means of a navigation system 16 allocates to the mobile microwave transmitting/receiving device installed in a vehicle the predetermined location for the specific surveillance task.

Once this location has been taken up, the transmitter 9.1 and the receiver 9.2 are switched on. The result of location comparison is fed at the same time to a gate circuit 8, which is also connected to the comparator unit 11. If the recognition signal quantities of the building concerned are verified by the comparator unit and if the microwave transmitting/receiving device 9 is in operation, the cyclical multiplexer 3 is stopped precisely at the memory address $Z_x$ which corresponds to the building specifically under investigation.

Consequently, if there is a firm degree of deviation between the model signal quantities 2.1, 2.3 and the actual signal quantity 10.1, for the purpose of issuing alarm information, the signal quantities 2.2 (security measures on establishing unauthorized use of the building) are displayed together with the positional data and building-specific additional information on the indicating or alarm-signalling device 7.

Practical results have shown that, surprisingly, in a frequency range from 1.3 to 1.6 GHz the microwave power required for measuring body signals through structural surrounds is particularly low, so that this frequency range is particularly well suited for a surveillance system.

Figure 1B:
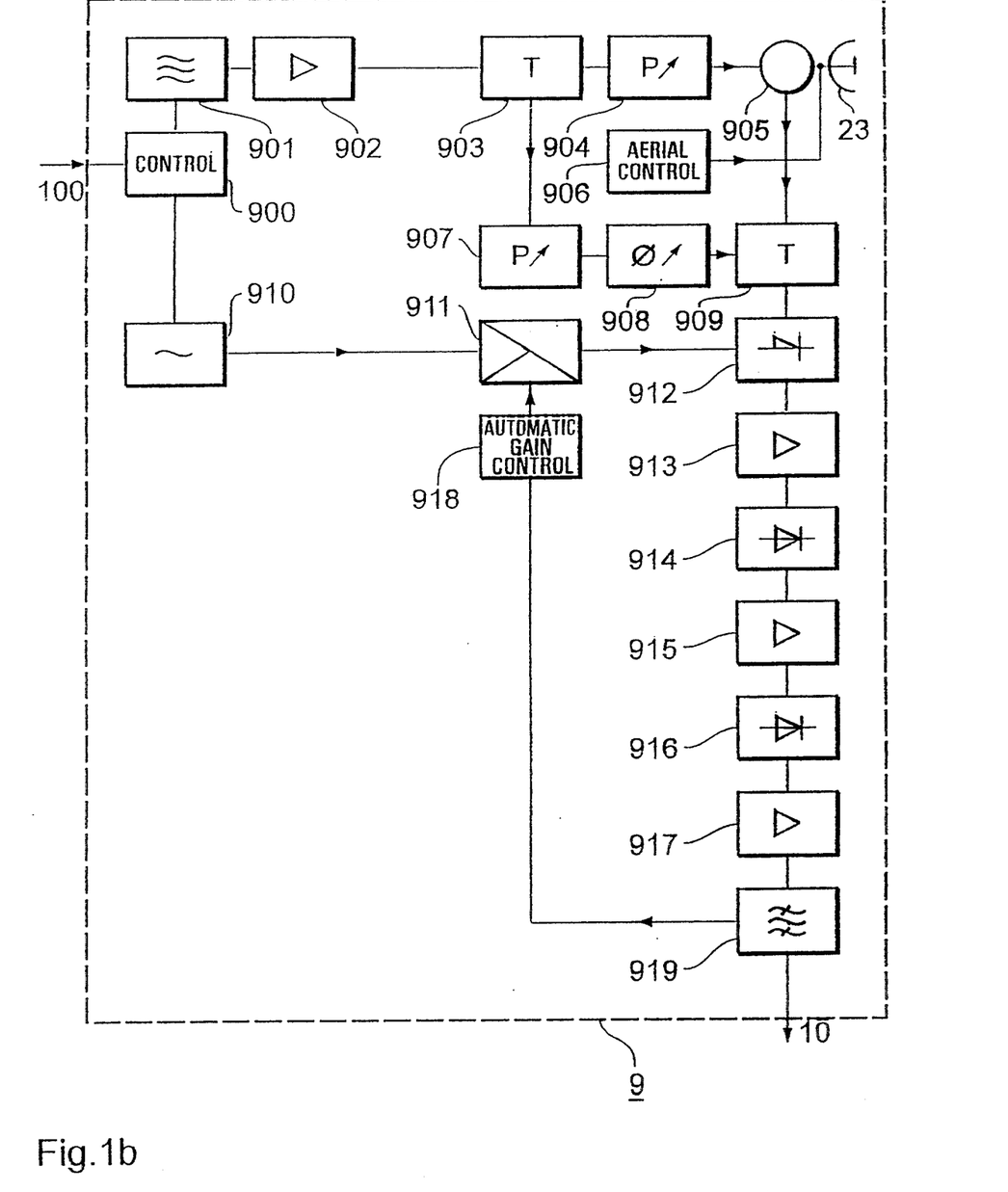
FIG. 1b shows the schematized representation of the microwave transmitting/receiving device shown in FIG. 1a, FIG. 1c shows the schematized representation of the signal processing device shown in FIG. 1b.

FIG. 1b shows the configuration of the microwave transmitting/receiving device 9 in details.

The device 9 is controlled by a control 900. In response to a corresponding command of the control 900 a microwave generator 901 emits a microwave signal with a power of 20 mW, which is fed to an amplifier 902, which amplifies it to a power of 200 mW. The output of the said amplifier is connected to a directional or voltage coupler 903, which branches off part of the signal power, while the main part is fed via a power control stage 904 to a circulator 905 and from the latter to a combined transmitting/receiving aerial 23, via which the microwaves are radiated into the area to be subjected to surveillance.

The aerial has a pronounced directional characteristic and is guided step by step over a spatial area to be subjected to surveillance—in dependence on the size of the area and the distance of the measuring vehicle from the latter—by an aerial control 906 known per se. The required data are fed to the aerial control from the comparator unit 15, which receives them in the way described above.

The microwave signals reflected from the area to be subjected to surveillance are received by the aerial 23 and passed to the directional or voltage coupler 909 where the component of the transmitted signal removed in the directional coupler 903 and adjusted in amplitude and phase in the attenuator 907 and the controllable phase shifter 908 is added to the received signal such that the unmodulated component of the received signal and the branched-off transmitted signal cancel each other out, so that only the modulated component of the received signal remains for further signal processing.

This signal is fed to a modulator 912, where it is modulated with a modulation voltage generated by an audio-frequency generator 910, likewise controlled by means of the control 900, and fed via an adding stage 911, the function of which is explained further below.

The signal passes via a microwave preamplifier 913, a demodulator 914, a narrow-band amplifier 915, a rectifier 916 and a low-frequency amplifier 917 to a branching point, from which it is fed on the one hand via a band-pass filter 919 finally to the second signal processing unit 10, on the other hand via an automatic gain control circuit 918 of the conventional type to the adding stage 911. There, it is impressed onto the modulation voltage which is then fed to the modulator 912.

The additional modulation of the modulated component of the microwave received signal with an audio-frequency voltage obtained in its amplitude by a feedback from the signal itself serves for automatically ensuring an optimum operating range of the stages 913 to 919 and consequently for improving the signal-to-noise ratio and for preventing overdriving in the signal preprocessing path, which would falsify the measured frequency spectra and consequently have terrible effects on the information value of the subsequently obtained actual signals.

Figure 1C:
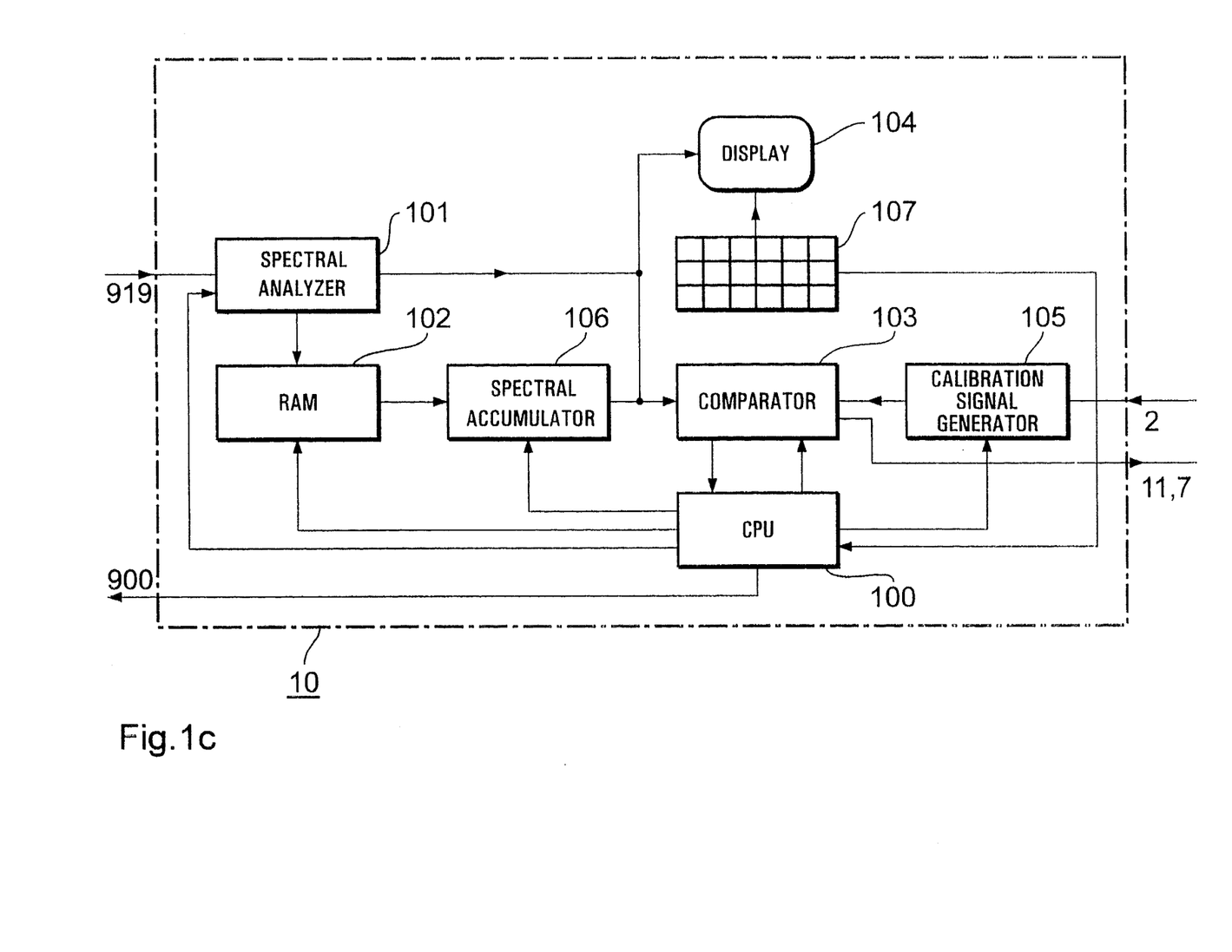

FIG. 1c shows a schematized construction of the signal processing unit 10 more precisely. The unit 10 is controlled by a control (CPU) 100, which also controls the control 900 of the transmitting/receiving device 9.

The signal from the band-pass filter 919 passes to a spectral analyzer 101 with digital signal processor hardware or software which executes in a known way a frequency analysis by fast Fourier transformation (FFT) of the signal for transforming from the time domain into the frequency domain. The transformed signal is at the same time stored in a RAM 102 and fed to a display 104 for visual display for the operator and to a comparator 103. The display 104 may in this case also be identical to the indicating device 7.

In the case of an embodiment designed especially for rescue tasks, the indicating device(s) of the life detection system is (are), moreover, also advantageously assigned an acoustic indicator, and/or optical indicator producing a clear signalling effect, for the reception of modulated signals—i.e. the accomplished detection of living persons—independently of their more precise evaluation. The drive signal for such a signal generator may be picked up after the band-pass filter 919 or after the spectral analyzer 101.

The comparator 103 also receives from a calibration signal generator 105 a signal of which the signal-to-noise ratio corresponds to a value required for correct further processing in the comparator 11. This signal is obtained, for example, from model signals 2.3 stored in the memory device 2.

If the signal-to-noise ratio of the measuring signal is less than that of the calibration signal, or than a predetermined minimum value, the comparator emits a signal identifying this fact to the CPU, which thereupon instructs the control 900 of the transmitting/receiving device to execute a further measuring operation. The measuring signal obtained as a result of this in turn passes into the spectral analyzer 101, the memory 102 (where it is deposited in a different memory location than the first measuring signal) and the display 104. However, at the initiation of the CPU 100, it does not pass directly to the comparator 103, but is fed jointly with the first measuring signal from the memory 102 to a spectra accumulator 106, known per se, where it is superimposed with the first measuring signal and, as a result, the signal-to-noise ratio is improved. The spectrum obtained in the spectra accumulator 106 is fed to the comparator and checked as to whether it has the required signal-to-noise ratio. If this is the case, the CPU 100 instructs the comparator 100 to output the spectrum to the comparator 11 and instructs the control 900 to wait for a new control command. If the signal-to-noise ratio is not yet adequate, the measurement is repeated and the measuring result accumulated until the required value has been reached or the operation is aborted.

An input device 107 serves for the abortion of the measuring operation and for the input of operator commands controlling the signal processing.

Figure 2:
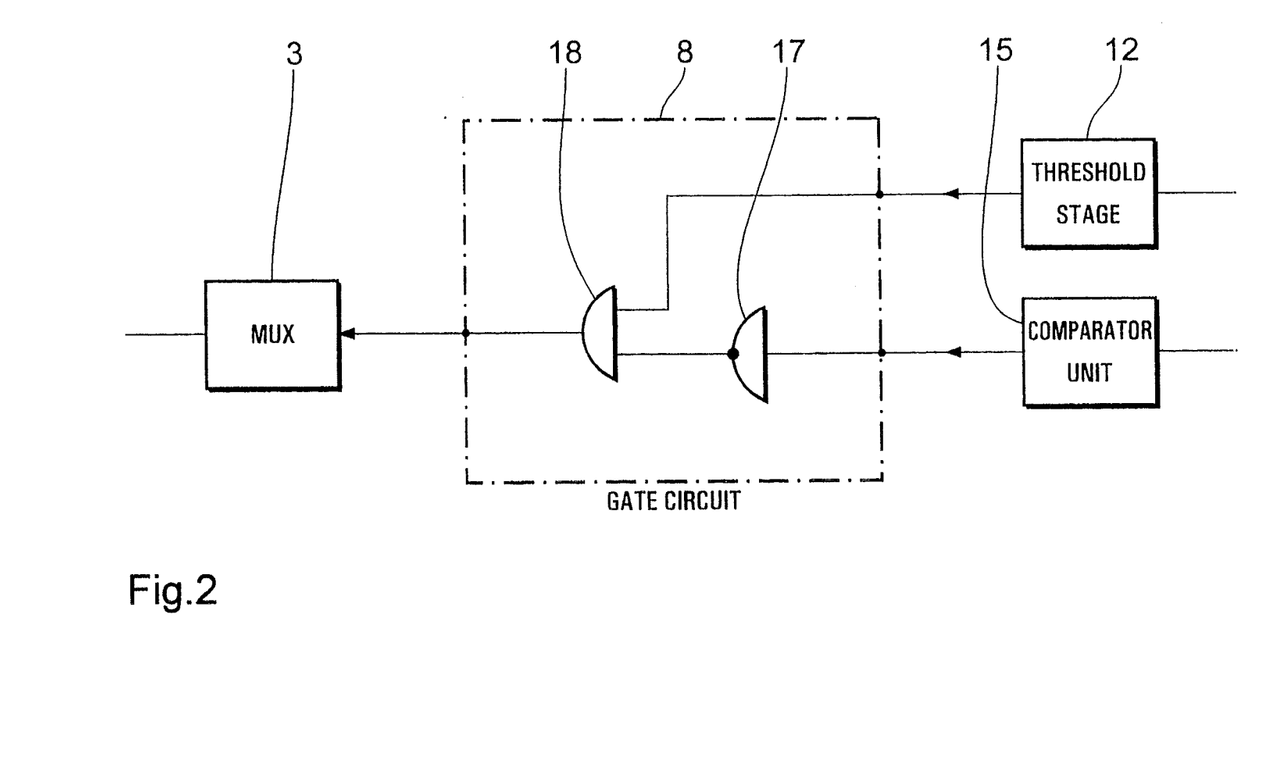
FIG. 2 shows the schematized representation of a detail of the embodiment of the invention shown in FIG. 1.

FIG. 2 shows an advantageous embodiment of the gate circuit 8 described in FIG. 1.

The gate circuit 8 includes an AND gate 18, the inputs of which are connected on the one hand directly to the threshold stage 12 of the first comparator unit (reference 11 in FIG. 1) and on the other hand via a negator 17 to the comparator unit 15 for the control of the measuring locations.

Once the correct location for the measuring has been taken up, i.e. model and actual recognition signal quantities of the spatial area to be investigated match, the AND gate 18 switches through, and the cyclical multiplexer 3 stops at the memory location $Z_x$ assigned to the spatial area currently to be subjected to surveillance of the first memory device (reference 2 in FIG. 1), the content of which can be displayed.

Figure 3:
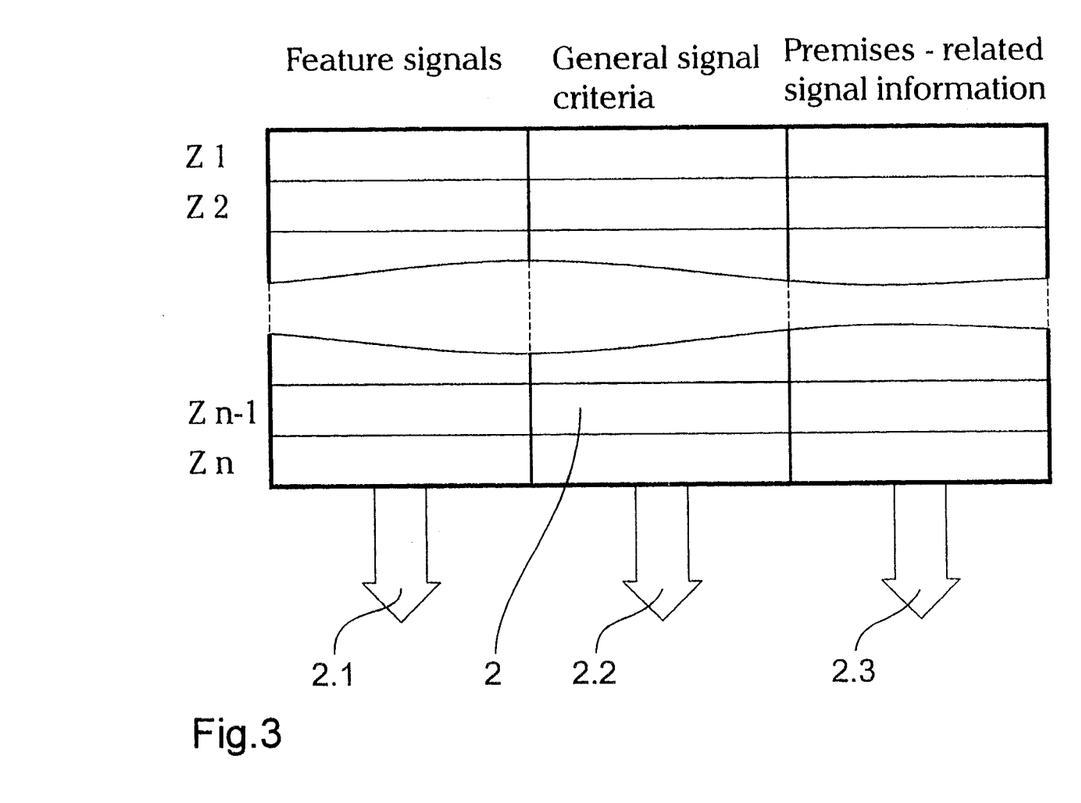
FIG. 3 shows the schematized representation of a first signal memory of the embodiment.
Figure 4:
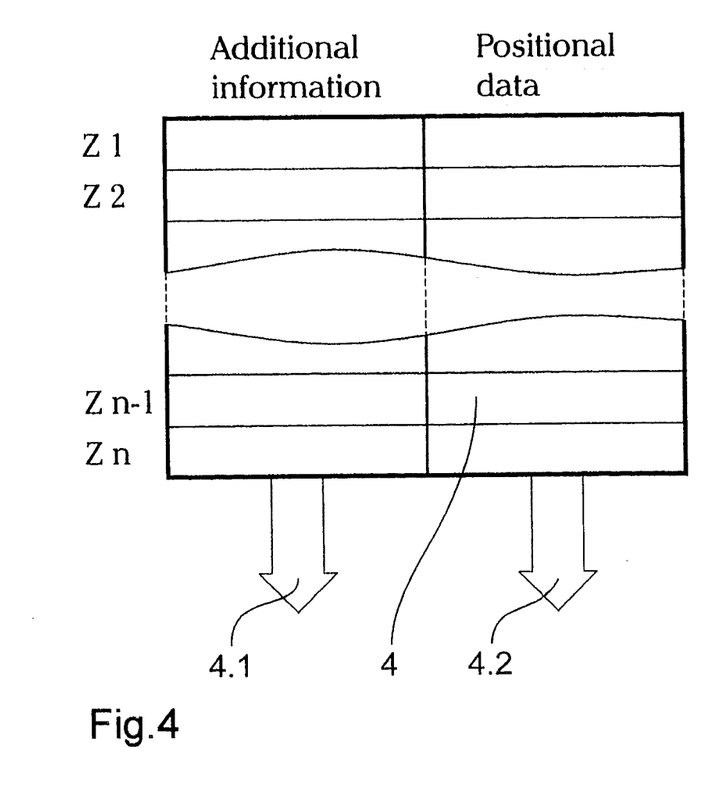
FIG. 4 shows the schematized representation of a second signal memory of the embodiment.

In FIGS. 3 and 4 the construction of the first and second memory devices 2 and 4 is represented in schematized form. For a surveillance area of n buildings, each of the two matrix memories contains n rows which are denoted by $Z_1$ to $Z_n$ and are respectively assigned to one of the buildings. The signal quantities 2.1, 2.2 and 2.3 relate—in this sequence—to building-specific features (feature signal), premises-related security measures (general signal criteria) and body-oscillation spectra of all persons or domestic animals normally present in the building. The matrix memory 4 likewise contains, row by row, assigned to the individual buildings, the positional data 4.2 and additional information 4.1, by which, for example, control times can be predetermined.

Figure 5:
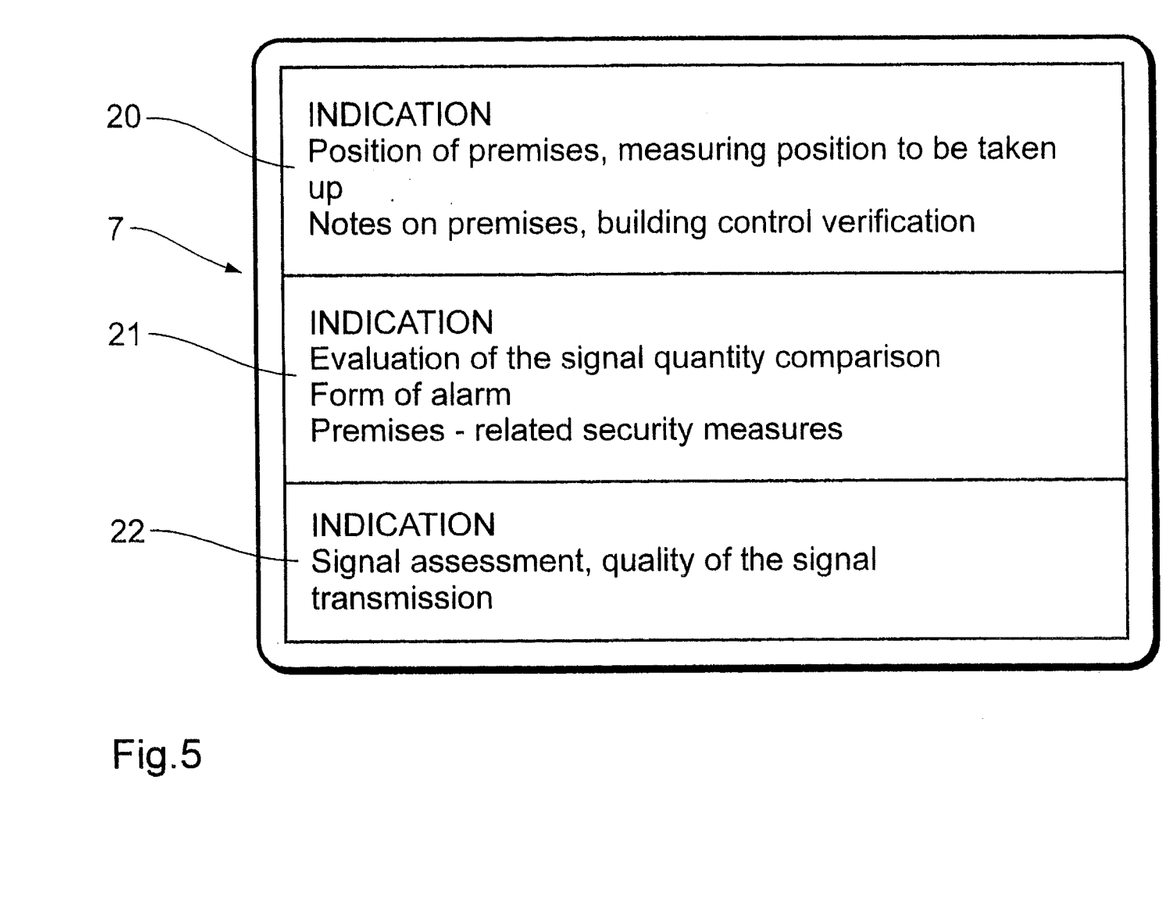
FIG. 5 shows an advantageous configuration of the display device corresponding to the embodiment and FIG. 6 shows a representation of detected signal data which, on the basis of the modulation of reflected microwave components, serve for the detection of persons or domestic animals.

A favourable form of representation of the result of surveillance and—in the event of an alarm—of alarm information is represented in FIG. 5 as a display of the indicating unit 7.

The display is divided into three indicating areas 20, 21, 22 in which textual information is respectively displayed. The upper area 20 is intended for an indication of the position of the building and the measuring locations to be taken up. At the same time, a control note on the surveillance respectively carried out is indicated (and stored). In the middle indicating area 21, there appears in the given case as a result of the evaluation of the model signal quantities with the actual signal quantities an alarm indication and a display of relevant security or else rescue measures which are to be carried out in the event of an alarm, taking into account special building-specific circumstances. The third display field 22 serves for indicating the quality of the signal transmission and consequently of the information on the requirement, if need be, for the surveillance operation to be repeated.

Figure 6:
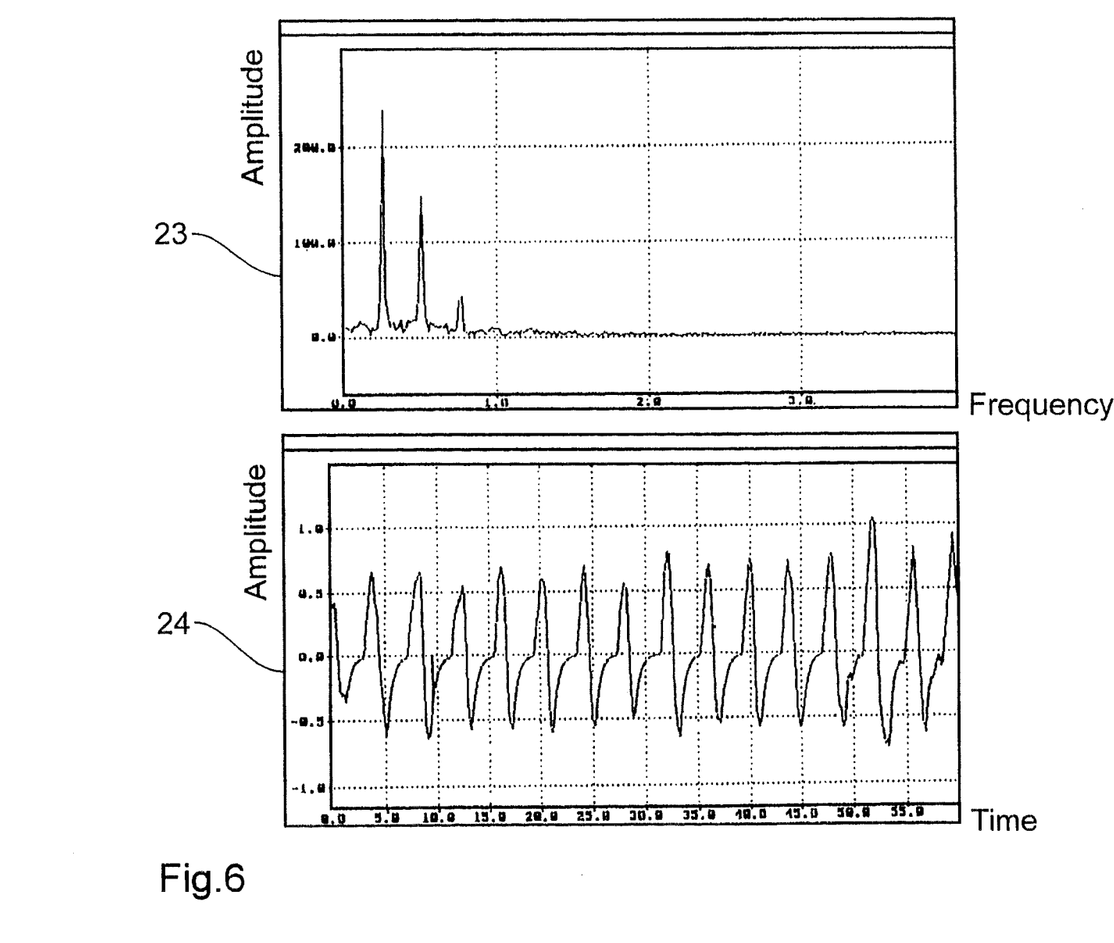

In FIG. 6, to illustrate the measuring principle, the measuring result of a direct microwave detection of the breathing of a person is represented in the form of a diagram. The amplitude-time diagram 24 shows the normal breathing rhythm of a male person for the time range of 1 minute. The frequency spectrum 23 derived from this waveform by means of a Fourier transformation shows in the first quarter of the represented normalised frequency range three characteristic peaks, the frequency position and amplitude value of which are specific to the individual person.

A refined measuring technique allows on this basis the preparation of individual, fingerprint-like body oscillations, the characteristic features of which—in particular frequency components from harmonics—allow the identification of a person even independently of their current breathing and heart rhythm. On this basis, the model signal quantity which is, for instance, underlying a surveillance includes the body-oscillation patterns of all persons and/or animals justifiably present in a building or section of a building in question. Within the scope of a reference measurement, in which all entitled persons are present in the building, the model signal quantity can be coherently determined or else synthesised from individual, separately recorded body-oscillation spectra of entitled persons. If frequency patterns which are atypical for the authorized persons occur in the measured actual signal quantity, this means the presence of an unauthorized person.

Similarly, information on the physical condition of detected persons—for instance avalanche or earthquake victims—can be obtained from the body-oscillation spectra even before they are saved, which permits a precise determination of the required rescue measures.

A metrologically less refined surveillance system within the scope of the invention comprises the assignment of an identifying signal generator to each person authorized to be present in a section to be subjected to surveillance, if need be also to domestic animals. Such an identifying signal generator emits an identifying signal which can be sensed by means of the microwave scanning of the area in question, is detected together with the body oscillations of the persons and/or animals authorized to be present in this area and identifies the said persons or animals in the frequency pattern as authorized persons or animals. If components without identifying signal assignment then occur in the frequency pattern, these are to be assigned to an unauthorized person or animal and result in an alarm being set off. In a specific development, the identifying signal generator is an infrasonic transmitter—expediently variable in its frequency—which delivers a characteristic frequency peak close to the body-oscillation fundamental frequencies, which is easily detectable by the microwave receiver.

In the case of this latter variant, no individual body-oscillation patterns have to be recorded from the authorized persons and/or animals and evaluated, instead a measuring device operating substantially in the range of the fundamental oscillations suffices.

A further development of the invention is that the surveillance system is not mobile but installed in a fixed place. This dispenses with some of the functional groups and process steps described in the above exemplary embodiment, in particular those associated with the correct localisation of the building to be subjected to surveillance and of the measuring vehicle.

In special configurations, it is also possible to dispense with a directional aerial and its control and to radiate and record the measuring signal by means of simple, even fixedly installed, metal surfaces.

What is claimed is:

1. Electronic life detection system using microwaves which are reflected to produce a reflected signal from a scanned area, the reflected signal having a portion modulated by body oscillations of a living being and an unmodulated portion, the system having a microwave transmitting/receiving device for generating and radiating the microwaves and also for receiving the reflected signal, the transmitting/receiving device having a first signal-conditioning device for conditioning a received reflected signal by elimination of the unmodulated portion the system also having an indicating device for outputting indication results, wherein the improvement comprises:

the first signal-conditioning device including a compensation loop and a control loop for controlling the amplitude of the modulated portion of the received reflected signal; and a second signal-conditioning device is arranged downstream of the microwave transmitting-/receiving device, said second signal-conditioning device subjecting the received reflected signal processed by the first signal-conditioning device to a frequency analysis.

2. System according to claim 1, characterized in that the second signal-conditioning device has a processing unit for the execution of a fast Fourier transformation and/or correlation analysis with respect to the modulated component of the received signal.

3. System according to claim 1, wherein the second signal-conditioning device has a device for the optional signal accumulation of a plurality of successively recorded received signals for the purpose of improving the signal-to-noise ratio.

4. System according to claim 1, wherein said first signal conditioning device comprises a compensation loop, by means of which the unmodulated transmitted signal is fed to the received signal with a delay and in phase opposition.

5. System according to claim 1, wherein said first signal-conditioning device has a generator for generating a modulation voltage, an automatic gain control, arranged downstream of modules for the amplification, demodulation and filtering of the modulated component of the received signal, an adding stage for mixing the output signals of the generator and of the gain control, and a modulator, arranged upstream of the modules for the amplification, demodulation and filtering, for additional modulation of the modulated component of the received signal with the output signal of the adding stage.

6. System according to claim 3, wherein said device for the optional signal accumulation has a second memory device for storing successively recorded, conditioned measuring signals, a calibration signal generator for supplying a signal stored in advance, serving as normal with respect to the signal-to-noise ratio, an adding stage for the accumulation of successively recorded measuring signals stored in the second memory device, a second comparator unit for the comparison of a conditioned measuring signal or of an output signal of the adding stage with the calibration signal and also a control for controlling the interacting of the second memory device, of the calibration signal generator, of the adding stage and of the second comparator unit as well as of the microwave transmitting/receiving device.

7. System according to claim 1, further comprising:
a first memory device for the storing and outputting of at least one model signal quantity, which describes a state serving as the normal state of the absence of certain living beings in the area to be investigated, and a first comparator unit for the comparison of an actual signal quantity, supplied by the second signal-conditioning device, and the at least one model signal quantity, output from the first memory device, with each other, which comparator unit outputs an output value quantity characterizing the deviation of the actual signal quantity from the model signal quantity.

8. System according to claim 1, wherein said second signal-conditioning device has a device for processing the actual signal quantity and the at least one model signal quantity by a correlation method.

9. System according to claim 1, wherein the microwave transmitting/receiving device is designed for a frequency range of substantially 1.3 to 1.6 GHz.

10. System according to claim 1, wherein the aerial of the microwave transmitting/receiving device has a pronounced directional characteristic and is able to be swivelled horizontally and/or vertically, in particular step by step.

* * * * *